(12) United States Patent
Fukuda et al.

(10) Patent No.: US 7,052,462 B2
(45) Date of Patent: May 30, 2006

(54) ULTRASONIC PROBE AND ULTRASONIC DIAGNOSTIC EQUIPMENT

(75) Inventors: Hiroshi Fukuda, Hachioji (JP); Masayoshi Omura, Saitama (JP)

(73) Assignee: Olympus Corporation (JP)

( * ) Notice: Subject to any disclaimer, the term of this patent is extended or adjusted under 35 U.S.C. 154(b) by 290 days.

(21) Appl. No.: 10/281,417

(22) Filed: Oct. 24, 2002

(65) Prior Publication Data

US 2004/0082858 A1   Apr. 29, 2004

(51) Int. Cl.
*A61B 8/12* (2006.01)

(52) U.S. Cl. ..................................... 600/445
(58) Field of Classification Search ........ 600/407–471; 252/62; 73/620–633; 367/3, 11, 30, 138; 128/916; 424/9.51, 9.52
See application file for complete search history.

(56) References Cited

U.S. PATENT DOCUMENTS 4,686,057 A * 8/1987 Lochner et al. ............... 252/62
5,400,788 A * 3/1995 Dias et al. ................... 600/459

* cited by examiner

*Primary Examiner*—Ali Imam
(74) *Attorney, Agent, or Firm*—Ostrolenk, Faber, Gerb & Soffen, LLP

(57) ABSTRACT

A flexible shaft is inserted through a sheath constituting an insertion portion of an ultrasonic probe connected to an ultrasonic observation apparatus, an ultrasonic transducer driven to rotate, etc., is attached at the distal end portion thereof, and an ultrasonic wave can be transmitted and received through an acoustic window arranged around thereof. By using hydrocarbon-based oil having a kinematic viscosity of 20 $mm^2/s$ as an acoustic medium for filling the surrounding of the ultrasonic transducer in the acoustic window, ultrasonic attenuation at high frequencies can be reduced, decrease of the capacity of the acoustic medium due to volatilization can be reduced, and decrease of the capacity of the acoustic medium due to volatilization is reduced.

7 Claims, 2 Drawing Sheets

ULTRASONIC PROBE AND ULTRASONIC DIAGNOSTIC EQUIPMENT

BACKGROUND OF THE INVENTION

1, Field of the invention

The present invention relates to an ultrasonic probe and ultrasonic diagnostic equipment provided with an ultrasonic transducer used for ultrasonic observation.

2, Related Art Statement

In an ultrasonic probe and an ultrasonic endoscope which produce an ultrasonic image by mechanically rotating or shaking an ultrasonic transducer, an acoustic medium which transmits an ultrasonic wave is allowed to fill in between the ultrasonic transducer and a sheath storing it or a cap.

Conventionally, liquid paraffin having low toxicity to a living body, water, carboxymethyl cellulose (CMC) aqueous solutions, and the like have been used as the acoustic medium.

However, conventional acoustic media in ultrasonic probes and ultrasonic scopes-which produced ultrasonic images by mechanically rotating or shaking ultrasonic transducers had problems as described below.

When water or an aqueous solution of carboxymethyl cellulose or the like is used as the acoustic medium, the acoustic medium is decreased with time due to volatilization of water and, therefore, the acoustic medium has to be periodically replenished.

When commonly used conventional liquid paraffin having a kinematic viscosity on the order of 70 mm$^2$/s is used as the acoustic medium, decrease of the capacity of the acoustic medium with time due to volatilization is reduced. However, regarding ultrasonic transducers of high frequencies of 10 MHz or more, since ultrasonic attenuation in the liquid paraffin is large, it is difficult to render adequate characteristics.

OBJECT AND SUMMARY OF THE INVENTION

It is an object of the present invention to provide an ultrasonic probe, in which ultrasonic attenuation at high frequencies is small and decrease of the capacity of an acoustic medium due to volatilization can be reduced, and ultrasonic diagnostic equipment using this ultrasonic probe.

An ultrasonic probe of the present invention is the ultrasonic probe for producing an ultrasonic image by mechanically driving an ultrasonic transducer, wherein hydrocarbon-based oil having a kinematic viscosity of 20 mm$^2$/s or less is used as an acoustic medium allowed to fill in between the ultrasonic transducer and an acoustic window which is in contact with an examined body and which transmits an ultrasonic wave.

To put it briefly, the ultrasonic probe of the present invention is the ultrasonic probe for producing an ultrasonic image by mechanically driving the ultrasonic transducer, and by using the hydrocarbon-based oil having a kinematic viscosity of 20 mm$^2$/s or less as the acoustic medium allowed to fill in between the ultrasonic transducer and the acoustic window which is in contact with a living body and which transmits an ultrasonic wave, the characteristic of ultrasonic attenuation at high frequencies can be reduced, an ultrasonic image at a significant ultimate depth can be produced and, in addition, decrease of the capacity of the acoustic medium due to volatilization can be reduced.

Ultrasonic diagnostic equipment of the present invention is provided with an ultrasonic probe with a built-in ultrasonic transducer, and displays an ultrasonic image by performing signal processing with respect to the aforementioned ultrasonic transducer, wherein hydrocarbon-based oil, having a kinematic viscosity of 20 mm$^2$/s or less, fills the surrounding of the aforementioned ultrasonic transducer to serve as an acoustic medium.

The above and other objects, features and advantages of the invention will become more clearly from the following description referring to the accompanying drawings.

DETAILED DESCRIPTION OF PREFERRED EMBODIMENTS

The present embodiments will be described with reference to the drawings.

Figure 1:
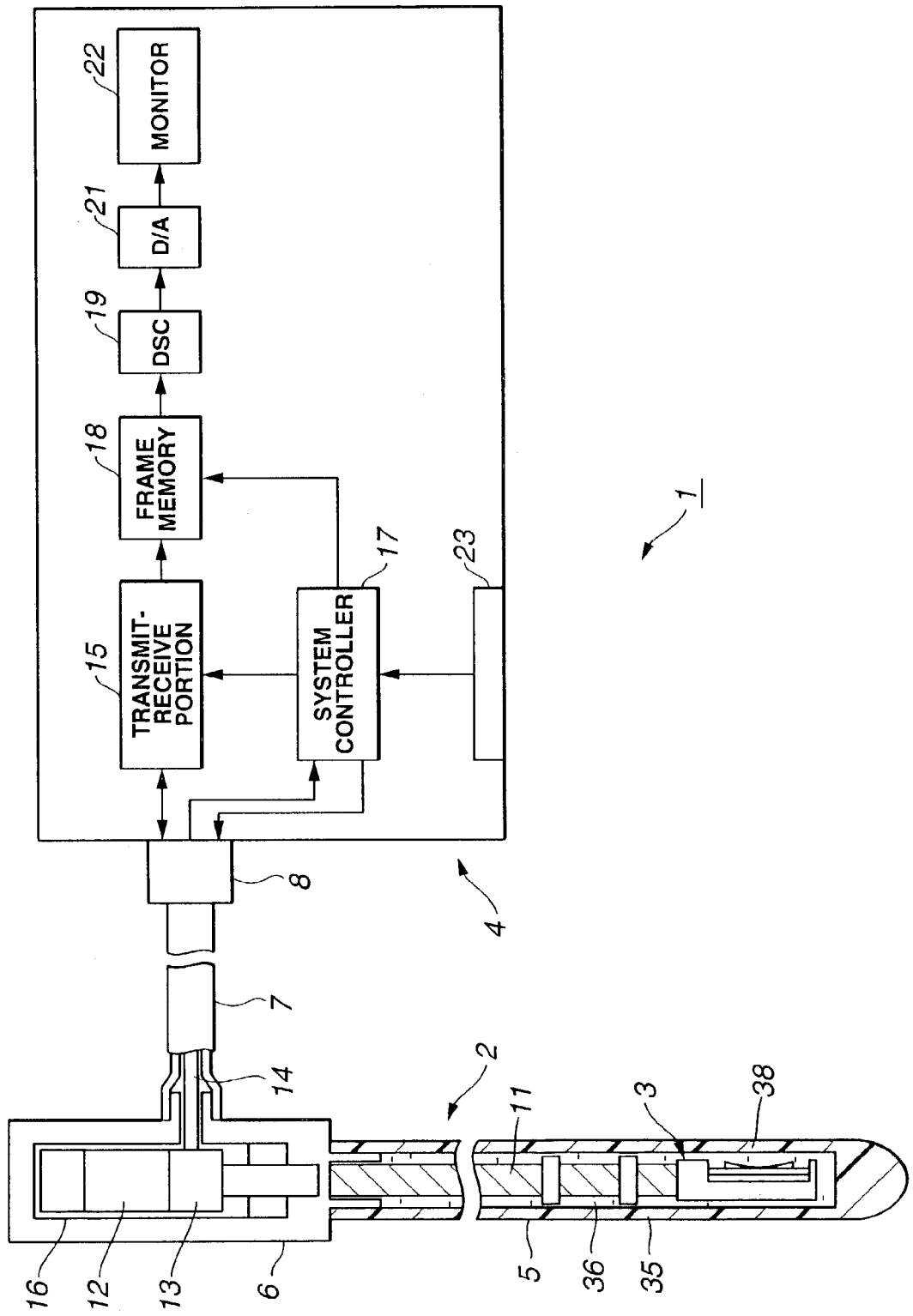
FIG. 1 is a block diagram showing the total configuration of ultrasonic diagnostic equipment provided with an embodiment of the present invention.
Figure 2:
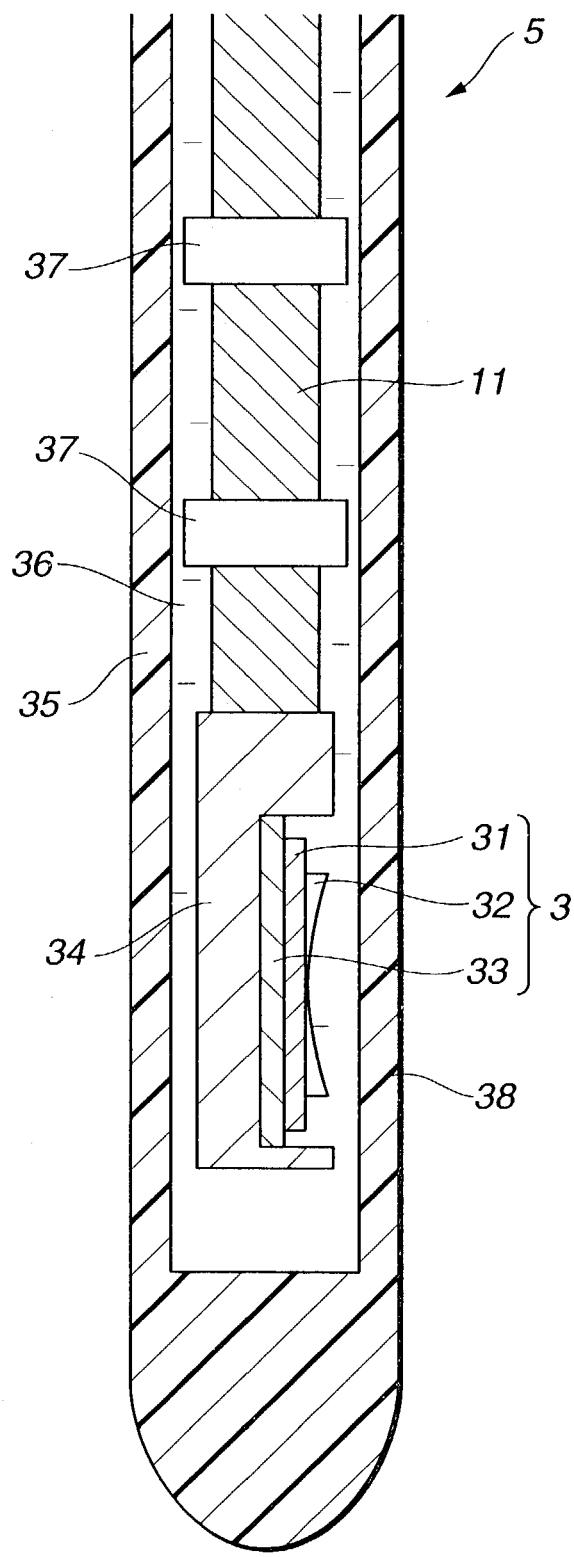
FIG. 2 is a sectional view showing the structure of the distal end portion of an ultrasonic probe.

FIGS. 1 and 2 relate to an embodiment of the present invention. FIG. 1 shows the total configuration of ultrasonic diagnostic equipment provided with the embodiment, and FIG. 2 shows the structure of the distal end portion of an ultrasonic probe.

As shown in FIG. 1, the ultrasonic diagnostic equipment 1 is composed of an ultrasonic probe 2 which is inserted into a body cavity, etc., so as to perform transmission and reception of the ultrasonic wave with respect to an examined body and an ultrasonic observation apparatus 4 which is connected to this ultrasonic probe 2 and which displays an ultrasonic image by performing signal processing with respect to an ultrasonic transducer 3 built in the ultrasonic probe 2 and the like.

The ultrasonic probe 2 includes a slender and flexible insertion portion 5 to be inserted into a body cavity, etc., a holding portion 6 arranged at the rear end of this insertion portion 5, a cable portion 7 extended from this holding portion 6, and a connector 8 arranged at the distal end portion of this cable portion 7. This connector 8 is connected to the ultrasonic observation apparatus 4 while being free to attach and detach.

A flexible shaft 11, for example, is inserted through the insertion portion 5 of this ultrasonic probe 2, and an ultrasonic transducer 3 is attached to the distal end portion of this flexible shaft 11. The back end of this flexible shaft 11 is connected to, for example, a motor 12 arranged in the holding portion 6, and by rotating this motor 12, the ultrasonic transducer 3 is driven to rotate together with the flexible shaft 11 and, therefore, radial scanning can be mechanically performed.

The ultrasonic transducer 3 is connected to a coaxial cable, although not shown in the drawing, this coaxial cable is connected to a slip ring 13 in the holding portion 6 via the hollow portion of the flexible shaft 11, and a cable 14 connected to the contact on the stator side of this slip ring 13 is connected to a transmit-receive portion 15 for performing transmission and reception in the ultrasonic observation apparatus 4.

The motor 12 and a rotary encoder 16 for detecting the rotation angle of this motor 12 are also connected to a system controller 17 in the ultrasonic observation apparatus 4 via the cable 14.

The system controller performs control of rotation of the motor 12 and control of transmission and reception, etc. The transmit-receive portion 15 applies a transmission signal (driving signal) to the ultrasonic transducer 3 in order that an ultrasonic wave is transmitted and, in addition, the ultrasonic wave reflected at the examined body side is received by the ultrasonic transducer 3, an echo signal converted into an electric signal is, for example, amplified, the resulting signal is converted into a digital signal by an A/D converter not shown in the drawing, and is written into a frame memory 18 on a temporary basis under the control of the system controller 17.

The echo signal data written into the frame memory 18 are sound ray data in the radial direction, and are converted into data of the rectangular coordinate system by a digital scan converter (abbreviated as DSC) 19. Subsequently, the data are output to a monitor 22 via a D/A converter 21 and, therefore, an ultrasonic image is displayed.

Furthermore, switches for variably setting the characteristic of STC, etc., are arranged on a front panel 23 of the ultrasonic-observation apparatus 4.

FIG. 2 shows the structure of the ultrasonic transducer 3 arranged at the distal end portion of the ultrasonic probe 2.

The ultrasonic transducer 3 is constituted of a plate-shaped piezoelectric transducer 31 having a piezoelectric property of performing electroacoustic transduction, an acoustic lens 32 which is made of, for example, an epoxy resin and which has a property of collecting sounds, and a backing layer 33 which is made of ferrite rubber and which attenuates ultrasonic waves. The acoustic lens 32 is arranged on the front of this piezoelectric transducer 31, and the backing layer 33 is arranged on the back of the piezoelectric transducer 31.

The backing layer 33 portion of this ultrasonic transducer 3 is adhered and fixed to a housing 34, and this housing 34 is attached to the distal end of the flexible shaft 11. Although not shown in the drawing, electrodes are arranged on both surfaces of the piezoelectric transducer 31, a signal electrode on the acoustic lens surface side is electrically connected to a ground line of a coaxial cable, although not shown in the drawing, drawn through the hollow portion of the flexible shaft 11, and an electrode on the backing layer 33 side is electrically connected to a signal line of the aforementioned coaxial cable. This coaxial cable is connected to the ultrasonic observation apparatus 4 via a connector 8.

The ultrasonic transducer 3 is configured to be allowed to rotate by rotating the flexible shaft 11 in a flexible sheath 35 which is made of, for example, polyamide elastomer, and which constitutes an outer sheath of the insertion portion 5.

In the present embodiment, polyamide elastomer is used as the material for the sheath 35. However, polymethylpentene, polyurethane, polyfluoroethylene, polyethylene, etc., can also be used.

An acoustic medium 36 composed of hydrocarbon-based oil having a kinematic viscosity of 20 mm$^2$/s or less is allowed to fill in between the ultrasonic transducer 3 and the sheath 35.

By using the hydrocarbon-based oil having a kinematic viscosity of 20 mm$^2$/s or less as the acoustic medium 36 for filling in between the ultrasonic transducer 3 and the sheath 35 as described above, even for an ultrasonic probe of 10 MHz or more, the time and effort for replenishing the acoustic medium due to volatilization can be omitted while ensuring adequate ultimate depth in contrast to the case of conventional liquid paraffin where a problem of shortage of the ultimate depth has been brought about because of large ultrasonic attenuation.

That is, it is found out that when the low-viscosity petroleum-based hydrocarbon oil is used as the acoustic medium 36, ultrasonic attenuation in the acoustic medium 36 is reduced compared with the case where the conventional high-viscosity liquid paraffin is used as the acoustic medium 36. By using this hydrocarbon-based oil having a kinematic viscosity of 20 mm$^2$/s or less as the acoustic medium 36, even in the ultrasonic probe of 10 MHz or more, the time and effort for replenishing the acoustic medium 36 due to volatilization can be omitted while ensuring adequate ultimate depth.

By arranging bearings 37 at the distal end portion of the flexible shaft 11, the ultrasonic transducer 3 can be driven to rotate without jouncing and, therefore, radial scanning can be performed.

An ultrasonic wave transmission window portion (acoustic window) 38 is arranged in the portion facing the ultrasonic transducer 3 on the distal end portion of the sheath 35.

The following Table shows ultrasonic attenuation factors of the petroleum-based hydrocarbon oil used in the present embodiment and the conventional liquid paraffin having a different viscosity. The measurement of the ultrasonic attenuation is performed at an ultrasonic frequency of 5 MHz.

TABLE

| | Kinematic viscosity mm$^2$/s | Density g/cm$^3$ | Sound velocity m/s | Ultrasonic attenuation dB/cm at 5 MHz |
|---|---|---|---|---|
| Petroleum-based hydrocarbon oil used in the present embodiment | 12–15 | 0.85 | 1400 | 1.19 |
| Conventional liquid paraffin | 74–77 | 0.87 | 1450 | 2.44 |

In this Table, the kinematic viscosity is indicated as 12 to 15 mm$^2$/s. However, when the kinematic viscosity is 20 mm$^2$/s or less, excellent characteristics are exhibited with respect to the prevention of ultrasonic attenuation, etc., compared with those in the conventional example.

As described above, the present embodiment is characterized in that by using as the acoustic medium 36 of the ultrasonic probe 2 the hydrocarbon-based oil having a kinematic viscosity of 20 mm$^2$/s or less and a property of being unlikely to volatilize, in transmission and reception of ultrasonic waves at high frequencies, ultrasonic attenuation in the acoustic medium 36 can be reduced and, therefore, an ultrasonic image having an excellent S/N at a significant ultimate depth can be produced.

Next, actions of the present embodiment will be described.

As shown in FIG. 1, when the ultrasonic probe 2 is connected to the ultrasonic observation apparatus 4, and a switch of ultrasonic transmission and reception, although not shown in the drawing, is turned to the ON position, the motor 12 is rotated and, therefore, the ultrasonic transducer 3 is driven to rotate via the flexible shaft 11.

The rotation thereof is detected by the encoder 16, and a transmission signal is applied from the transmit-receive portion 15 to the piezoelectric transducer 31 of the ultrasonic transducer 3 in synchronization with the rotation. An ultrasonic wave is excited by this piezoelectric transducer 31, and the ultrasonic wave is sent out in the shape of a pulse while being converged by the acoustic lens 32.

This ultrasonic wave is propagated through the acoustic medium 36, and is passed through the ultrasonic wave transmission window portion 38 facing the ultrasonic transducer 3 in the sheath 35. The ultrasonic wave is emitted onto the examined body side in contact with this ultrasonic wave transmission window portion 38, and is reflected at the portion at which acoustic impedance changes on the examined body side.

The reflected ultrasonic wave is moved along a return route which is the reverse of the approach route, and is received by the piezoelectric transducer 31 so as to convert into an electric signal, that is, an echo signal. The resulting signal is detected and amplified by the transmit-receive portion 15 and, thereafter, A/D conversion is performed so that each of sound ray data (ultrasonic data) is stored sequentially in the frame memory 18.

The sound ray data are converted into sound ray data of the rectangular coordinate system by the DSC 19, and the resulting data are converted into an analog video signal by the D/A converter 21. The resulting signal is output to a monitor 22 together with an synchronizing signal not shown in the drawing and, therefore, an ultrasonic image is displayed on the display screen of the monitor 22.

In the present embodiment, since the acoustic medium 36 which exhibits reduced ultrasonic attenuation at high frequencies and which has a property of being unlikely to volatilize is used, the piezoelectric transducer 31 can get ultrasonic data having an excellent S/N compared with that in the conventional example. Consequently, an ultrasonic image having excellent quality at a significant ultimate depth can be produced and, in addition, there is an effect that it is possible to use stably for a long time without replenishment of the acoustic medium 36.

For example, when used for the acoustic medium 36 in the ultrasonic probe 2 of high frequencies having a center frequency of 10 MHz or more, an image with high resolution by high frequencies at a significant ultimate depth can be produced. Furthermore, since the volatility is low, it is possible to use without periodical replenishment for a long time.

In the above description, the case where the ultrasonic transducer 3 is driven to rotate is explained. However, it is clear that the ultrasonic transducer 3 is driven to shake is possible. Furthermore, application to the case of driving to rotate in a spiral is also possible.

As described above, the present embodiment has an significant effect on the case where the ultrasonic transducer 3 is mechanically driven, although may be applied to the case of electronic scanning.

In the present embodiment, the case where the ultrasonic probe 3 is provided with the ultrasonic transducer 2 at the distal end of the probe is described, but it is not limited to this, as a matter of course. For example, in an ultrasonic endoscope provided with an endoscope function, that is, optical observation means (optical system illumination means and optical observation device or image pickup means), in addition to the ultrasonic transducer at the distal end portion of the probe, the aforementioned acoustic medium 36 may be adopted around the ultrasonic transducer as well.

Having described the preferred embodiments of the invention referring to the accompanying drawings, it should be understood that the present invention is not limited to those precise embodiments, and various changes and modifications thereof could be made by one skilled in the art without departing from the spirit or scope of the invention as defined in the appended claims.

What is claimed is:

1. An ultrasonic probe for producing an ultrasonic image by mechanically driving an ultrasonic transducer, wherein:
   hydrocarbon-based oil having a kinematic viscosity of 20 mm$^2$/s or less is used as an acoustic medium to be filled in between the ultrasonic transducer and an acoustic window which is in contact with an examined body and which transmits an ultrasonic wave.

2. The ultrasonic probe according to claim 1, comprising:
   a function of an endoscope provided with optical observation means in the neighborhood of the ultrasonic transducer.

3. An ultrasonic probe for producing an ultrasonic image by mechanically driving an ultrasonic transducer, wherein:
   hydrocarbon-based oil exhibiting small ultrasonic attenuation in high frequency regions and having a kinematic viscosity of 20 mm$^2$/s or less is used as an acoustic medium to be filled in between the ultrasonic transducer and an acoustic window which is in contact with an examined body and which transmits an ultrasonic wave.

4. The ultrasonic probe according to claim 3, wherein:
   the high frequency regions are from 3 MHz to 50 MHz.

5. The ultrasonic probe according to claim 3, comprising:
   an endoscope function provided with an optical observation means in the neighborhood of the ultrasonic transducer.

6. Ultrasonic diagnostic equipment which comprises an ultrasonic probe with a built-in ultrasonic transducer and which displays an ultrasonic image by performing signal processing with respect to the ultrasonic transducer, wherein:
   the surrounding of the ultrasonic transducer is filled with hydrocarbon-based oil having a kinematic viscosity of 20 mm$^2$/s or less to serve as an acoustic medium.

7. Ultrasonic diagnostic equipment comprising an ultrasonic probe for producing an ultrasonic image by mechanically driving an ultrasonic transducer wherein:
   the ultrasonic probe uses hydrocarbon-based oil having a kinematic viscosity of 20 mm$^2$/s or less as an acoustic medium to be filled in between the ultrasonic transducer and an acoustic window which is in contact with an examined body and which transmits an ultrasonic wave.

* * * * *